(12) United States Patent
Hoenes et al.

(10) Patent No.: US 8,373,851 B2
(45) Date of Patent: Feb. 12, 2013

(54) MEASURING SYSTEM AND MEASURING METHOD, IN PARTICULAR FOR DETERMINING BLOOD GLUCOSE

(75) Inventors: Joachim Hoenes, Zwingenberg (DE);
Frederic Wehowski, Hockenheim (DE);
Reinhold Mischler, Ludwigshafen (DE);
Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/540,001

(22) Filed: Jul. 2, 2012

(65) Prior Publication Data

US 2013/0003043 A1    Jan. 3, 2013

Related U.S. Application Data

(63) Continuation of application No. PCT/EP2011/051168, filed on Jan. 27, 2011.

(30) Foreign Application Priority Data

Jan. 28, 2010    (EP) .................................... 10152018

(51) Int. Cl.
*G01N 33/48* (2006.01)
(52) U.S. Cl. ........................................... 356/39; 356/40
(58) Field of Classification Search ............... 356/39–42
See application file for complete search history.

(56) References Cited

U.S. PATENT DOCUMENTS

| | | | |
|---|---|---|---|
| 3,647,299 A | 3/1972 | Lavallee | |
| 5,089,229 A | 2/1992 | Heidt et al. | |
| 6,697,655 B2 | 2/2004 | Sueppel et al. | |
| 6,828,599 B2 | 12/2004 | Kim | |
| 2002/0030292 A1* | 3/2002 | Tasaki et al. | 264/21 |
| 2003/0058450 A1 | 3/2003 | Mosley et al. | |
| 2008/0291455 A1 | 11/2008 | Holland | |
| 2011/0075105 A1* | 3/2011 | Ouyang et al. | 353/31 |

FOREIGN PATENT DOCUMENTS

| | | |
|---|---|---|
| WO | WO 96/41138 | 12/1996 |
| WO | WO 99/12021 | 3/1999 |
| WO | WO 2005/020805 | 3/2005 |
| WO | WO 2006/037985 | 4/2006 |
| WO | WO 2010/038024 | 4/2010 |

OTHER PUBLICATIONS

International Preliminary Report on Patentability, International Application No. PCT/EP2011/051168, 11 pages.
Yasuyuki Okamura et al., Characteristics of Modulated White-LED and Their Application to Electrically Controlled Spectroscopy, Proceedings of SPIE, 2002, pp. 43-50, vol. 4922, XP-002558253, Copyright 2002 SPIE.

* cited by examiner

*Primary Examiner* — Michael P Stafira
(74) *Attorney, Agent, or Firm* — Krieg DeVault LLP

(57) ABSTRACT

A measuring system for determining blood glucose includes a photometric measuring unit with a light source and a detector, and an analytical test element, to which a body fluid sample can be applied, and which can be placed in a beam path between the light source and the detector for optical detection of an analyte. For an improved multi-wavelength measurement, it is proposed that the light source includes a first emitter that can be actuated in a first wavelength range to emit pulsating alternating light and a second emitter that can be excited in a second wavelength range to emit fluorescent light.

19 Claims, 2 Drawing Sheets

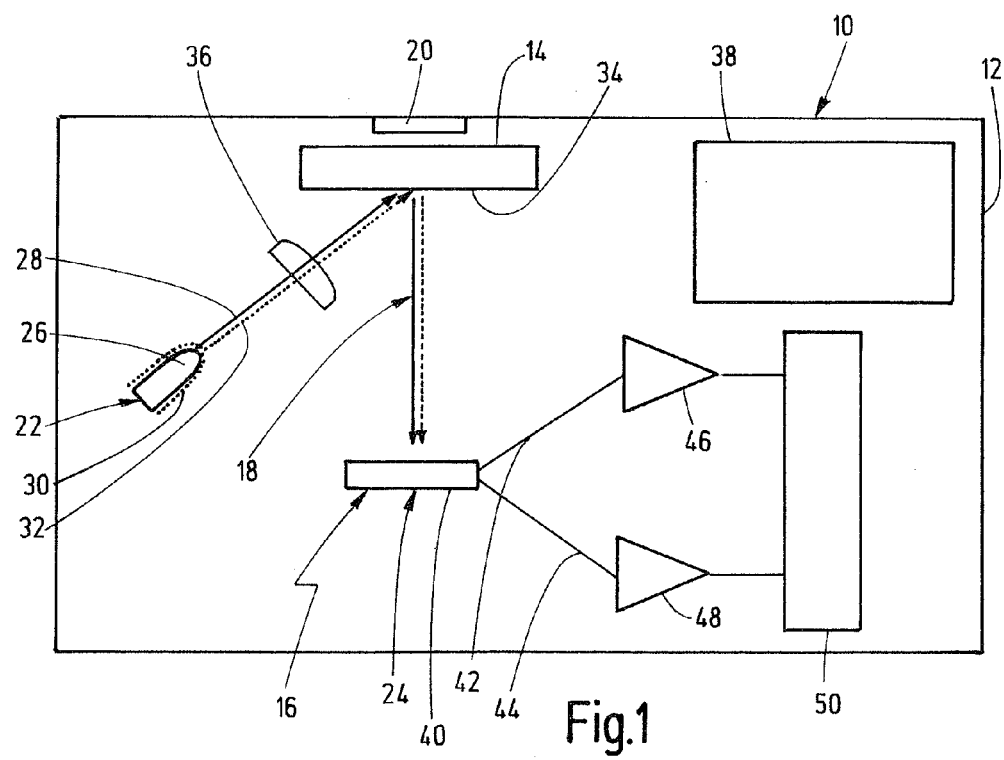
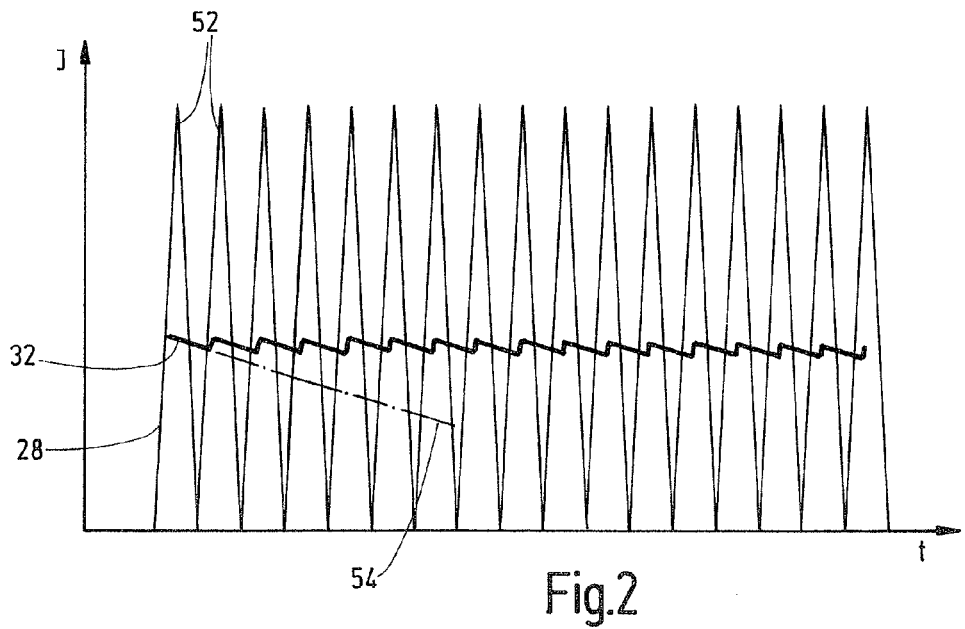

MEASURING SYSTEM AND MEASURING METHOD, IN PARTICULAR FOR DETERMINING BLOOD GLUCOSE

CROSS-REFERENCE TO RELATED APPLICATIONS

This application is a continuation of International Application No. PCT/EP2011/051168 filed Jan. 27, 2011, which claims priority to EP Application No. 10152018.7 filed Jan. 28, 2010. Each of the referenced applications is incorporated herein by reference in its entirety.

FIELD OF THE INVENTION

The invention relates to a measuring system, in particular for determining blood glucose, having a photometric measuring unit comprising a light source and a detector, and an analytic test element to which a sample can be applied, in particular a body fluid, and which, for an optical detection of an analyte, can be placed in a beam path between the light source and the detector. Moreover, the invention relates to a corresponding measuring method.

BACKGROUND

In the practice of determining blood glucose, known photometric measuring systems are based on irreversibly reacting carrier-bound test elements in the form of test strips or test tapes. These are intended to enable also the layperson to measure blood glucose by means of processing in automated compact hand-held devices, outside of a laboratory environment, with sufficient precision as required in the medical treatment of diabetes. The measuring process provides that, after the application of a blood sample, the analyte concentration is determined by means of appropriately repeated photometric measurements. For this, it is important that changes in the boundary conditions of the measurement are detected independently of the actual detection of the analyte.

SUMMARY

Systems and methods are disclosed herein for improving the devices and methods known in the prior art, and in particular the quality and precision of the measuring processes, wherein, with limited expenditure, an efficient and compact system is to be obtained.

Accordingly, it is disclosed herein with regard to a measuring system, that the light source contain a first emitter that can be actuated in a first wavelength range to emit a pulsed alternating light, and a second emitter, excited in a second wavelength range, for emitting fluorescent light. In this manner, a compact and efficient multi-wavelength light source can be obtained, which emits radiation that can be controlled in various wavelength ranges, and allows for a selective signal evaluation. In this manner, it is also possible to simultaneously execute an analyte and a control measurement in order to be able to ensure the necessary measurement quality.

For selective signal detection, in one embodiment the alternating light has a pulse duration, the fluorescent light decays with a fluorescence life cycle, and the fluorescence life cycle is multiple times greater than the pulse duration. By this means it is possible to use different life cycles or decay periods within the various wavelength ranges for the electronic selection instead of an elaborate wavelength selection through filters or the like.

Another embodiment provides that the first emitter takes the form of a light emitting diode which emits light, in particular, in the UV range. In a further embodiment the second emitter takes the form of a fluorescent substance that is optically excited by means of the pulsating first emitter to deliver, in particular, visible fluorescent light. Light emitting diodes have high degrees of light density and can, therefore, be used effectively to form intensively bundled light beams. By means of the combination with a fluorescent substance, it is possible to eliminate the need for numerous individual LEDs placed at various locations, which can only be bundled to form a homogenous light beam by means of an elaborate process.

In one embodiment both emitters are oriented collectively via a unified optical transmission path or beam path onto a measuring surface of the test element. Another embodiment, particularly regarded as to necessary structural space, is obtained wherein the second emitter is applied as a fluorescent phosphor layer to an emission surface of the first emitter, such that both light components can be generated by means of a single structural component.

In another embodiment, the detector includes a light receiver for the collective detection of alternating and fluorescent light and two amplifier channels for the wavelength-selective determination of measurement values.

For time-resolved separate detection of a pulsed light signal component generated by the alternating light, in another embodiment the detector has a lock-in amplifier that can be modulated with the pulse frequency of the alternating light.

It is also contemplated for the signal processing that the detector comprises an amplifier, in particular, an amplifier that functions as an integrator, for detecting a composite signal generated by means of the pulsed light and the fluorescent light, and a signal processor for determining the signal components of the alternating light and/or the fluorescent light, in particular for subtracting the pulsed light signal component from the composite signal.

For measurements conducted by the patient on-the-spot, it is disclosed that the measuring unit is integrated in a hand-held device and that the test element is configured as an disposable item for single use in the hand-held device.

The test element is disposed as a reflector in the beam path between the light source and the detector for a reflection photometric measurement, and in one embodiment allows for the photometric detection of an analyte in the sample by means of a reagent layer that comes in contact with the sample. For this purpose, the test element can have a receiving region for the application of the sample, while, if applicable, a measurement zone of the test element, separate or facing away on the rear of the receiving region, receives the radiation from the emitters of the light source, reflecting said radiation towards the detector, such as in a scattering manner. The optical characteristics of the test element are modified by the sample or, respectively, an analyte contained therein, thus resulting in a correspondingly modified measurement signal.

A particular embodiment is disclosed that provides that the test element is coupled with the light source by means of an optical unit, in particular an optical fiber, and that the optical connection is monitored by means of a separate signal evaluation in one of the wavelength ranges. A light source that is as small as possible is necessary for coupling the light into thin optical fibers in order to achieve high coupling efficiency. It should be noted that multiple separate LEDs can only be coupled while suffering a high degree of loss.

In terms of the method, a first emitter of the light source is actuated in a first wavelength range to emit pulsed alternating light, and a second emitter is excited in a second wavelength to emit fluorescent light superimposed onto the alternating light.

In this process, a signal component associated with the alternating light can be detected by means of time-resolved signal detection, such as by means of a lock-in amplifier. Another aspect is derived where in one wavelength range a value for an analyte in the sample is measured, and in another wavelength range a control value for the optical coupling of the test element to the measuring unit is measured.

BRIEF DESCRIPTION OF THE FIGURES

In the following, the invention shall be explained in greater detail with reference to the embodiments schematically depicted in the drawings.

FIG. 1 is a circuit diagram of a measuring system for measuring blood glucose with a multi-wavelength photometer.

FIG. 2 is a graph of a temporal curve of the beam intensity of a pulse emitter and a fluorescent emitter of the photometer according to FIG. 1.

DETAILED DESCRIPTION

Figure 3:
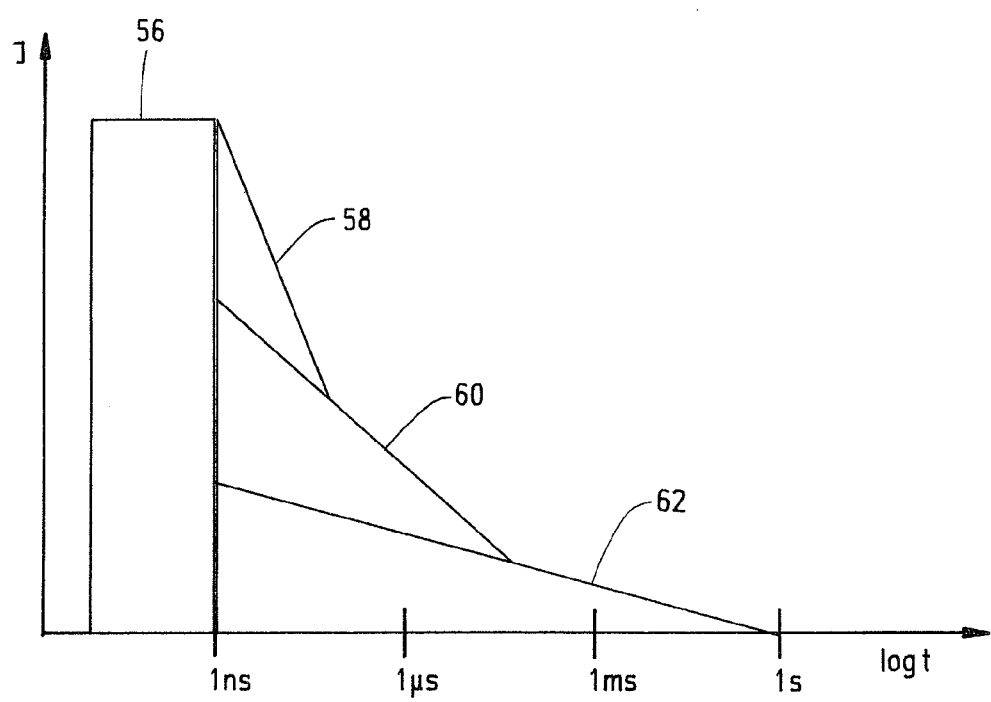
FIG. 3 is a graph of the beam intensity on a logarithmic time scale for another embodiment of a multi-wavelength measurement.

The measuring system 10 depicted in FIG. 1 comprises a portable test device 12 and test elements 14 that can be inserted therein, each to be used for a one-time test on a sample, specifically for the blood glucose determination in a blood sample. For this purpose, the test device 12 features a photometric measuring unit 16 in the beam path 18 of which a disposable test element 14, for example, in the form of a test strip or test tape can be placed, wherein a direct application of the sample to the test element 14 is possible by means of a support take-up 20 for a body part. The test element 14 is provided with a dry chemical reagent layer, which reacts to an analyte (e.g. glucose) with a color change that can be measured photometrically. The reagent layer can be applied to a transparent carrier as a distinct testing field.

The photometric measuring unit 16 comprises a multi-wavelength light source 22 and a two-channel detector 24. A first pulsed emitter 26 of the light source 22 is operated for emitting pulsed alternating light 28, while a second fluorescent emitter 30 is excited by the light of the first emitter 26 to emit fluorescent light 32, which has a longer wavelength. The first emitter 26 is constructed for this purpose as a light emitting diode producing light in the UV range, and the second emitter is constructed as a fluorescent layer applied to the light emitting diode, emitting light in the visible wavelength range. In this manner, both emitters 26, 28 can be powered as a single component, and oriented collectively towards a measuring surface 34 of the test element 14. A convergent lens 36 and/or an optical fiber can be provided for bundling the light onto a smallest possible measuring spot in the shared optical transmission path of the two emitters.

In order to detect changes in the state of the optical coupling of the test element 14 and to check the optical transmission behavior, a control value can be determined by means of the fluorescent light, while the UV light that responds to the analyte enables the determination of a measurement value which can be displayed in a digital format on the display 38 as concentration data for a user.

The determination of the control value allows for the detection of any unintended influence on the measurement conditions due to any device-side actuation or interference on the part of the user in the course of the preparation of the test element. For example, due to the application of pressure to the test element 14 by a body part, the sample can be subjected to an unintentional deformation or displacement. In addition, the detection of the measurement value at the initiation of the sample application is uncertain or imprecise, because the wetting of the test field does not occur abruptly in a homogenous manner, and the optical properties are subject to change. In order to remedy this, by means of a dual-wavelength measurement, the necessary measurement precision and stability with regard to disturbances can be ensured, using a limited amount of equipment.

For this purpose, the detector 24 has photoreceptors 40 that are sensitive in both wavelength ranges and two amplifying stages, or channels, 42, 44 connected thereto for the wavelength-selective determination of a measurement value. A lock-in amplifier 46 is disposed in a first amplifying stage 42 for time-resolved detection of an alternating light signal component. An integrating amplifier 48 for the integrated detection of a composite signal generated by the alternating light and the fluorescent light is located in the second amplifying stage. A subsequent signal processor 50 allows for the subtraction of the alternating light signal component from the composite signal and thereby the separate detection of the fluorescent light, or continuous light, signal component.

As can be seen in FIG. 2, the first emitter 26 can be actuated by means of quick current pulses, in microsecond cycles, for example, for emitting pulsed alternating light. The UV light 28 is generated almost instantly by the current pulses, resulting in individually resolvable light pulses 52 having a pulse duration of 1 µs. The fluorescent light of the second emitter excited thereby cannot, however, follow this frequency, as it decays with a significantly longer time constant. In the depicted example, the signal decline for a fluorophore used as the fluorescent layer 30 having a fluorescent life cycle, of e.g. 20 µs, is illustrated by the dashed/dotted curve 54. An example is the commercially available fluorophore of brand name Lumilux CD 163 from Honeywell, which emits fluorescent light at max. 517 nm in the green spectral range. Due to the quick pulse sequence and the relatively long fluorescence life cycle, the signal decline is shortened correspondingly, such that a continuous light component having only a limited periodic and random deviation is observed. Therefore, a quick pulsation of the short wave light 28 is superimposed by this means with a nearly constant continuous light of the fluorescent light 32 having a longer wavelength. Because it is possible to differentiate between the continuous light component and the pulsing light component during the detection, it is possible to measure the different light components emitted by the two emitters 26, 28 separately and without the use of wavelength filters or the like.

The measurement of the alternating light component is possible, in a particularly simple manner, by means of the lock-in amplifier 46. For this, a reference signal having the frequency of the modulated UV light is generated and adjusted to its phasing by means of a phase shifter. As an alternative to a phase shifter, a so-called double-lock amplifier can also be used, which can detect the alternating light, independently of the phasing, by means of a double measurement at the phasings of 0 and 90 degrees. The actual measurement signal is then multiplied with the reference signal by means of a multiplier, such that only the alternating light component of a finite output signal is delivered and the main component of the green continuous light is not detected therein.

A signal integration by means of the amplifier 48 over a longer time period results in the sum of UV light 28 and green light 32. A simple algorithm in the signal processor 50 can then subtract the alternating light component from the composite signal, thereby obtaining a separate measurement value for the continuous light component.

As a rule, it is not necessary to entirely separately detect alternating light and continuous light having very strongly differing frequencies. Even with frequencies that are closer together, two different signals are obtained having different portions of the two wavelengths, which can be determined by solving a system of equations (two equations with two variables). The integrator can be replaced with an amplifier having an appropriate different frequency, and the processor need not be limited to a simple subtraction.

As is shown schematically in the following table, the multi-wavelength measuring principle explained above can be expanded to more than two wavelengths or luminous colors with the appropriate decay periods gradated by fluorphores. For this, the frequency corresponding to ten times the decay period is given as the cut-off frequency for obtaining a high pulse amplitude.

TABLE 1

| Wavelength | Decay Period | Cut-off Frequency |
| --- | --- | --- |
| Ultraviolet | 10 ns (LED) | 10 MHz |
| Blue | 1 µs (LUMILUX blue) | 100 kHz |
| Green | 100 µs (LUMILUX green) | 1 kHz |

The alternating light of 10 MHz thereby contains only the UV intensity, the alternating light of 100 kHz contains the total amount of UV and blue light, while at frequencies of 1 kHz and less, the cumulative light intensity is detected.

The measurement can also be executed in accordance with FIG. 3 in that a rectangular light pulse 56 is generated by means of a current pulse, and its decay is analyzed. In the individual time ranges of the logarithmic time scale it is possible to separately measure the respective decays of each wavelength range 58, 60, 62. This method corresponds to the measuring method that is known per se for the determination of fluorescent life cycles. The exponential decay curve is adjusted thereby with one, two or three fluorescent life cycles and the corresponding intensity components as adjustment parameters. In the present application, the characteristic life cycles in the three wavelength ranges 58, 60, 62 are known in advance. Therefore, an adjustment can be executed with only three parameters, specifically the three intensity components in the respective wavelength ranges. The UV radiation follows the decay of the LED, and the decay curves of the fluorophore follow the fluorescence life cycles, which, for practical purposes, are selected as sufficiently different by a factor of at least 3, for example. For this, one must weigh the advantages of the possibility of sharper wavelength differentiation as a result of greater life cycle differences against an increased measuring period obtained as a result of an increased decay period.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A measuring system, comprising:
a photometric measuring unit comprising a light source and a detector; and
an analytical test element to which a sample of body fluid can be applied and which can be placed in a beam path between the light source and the detector for optical detection of an analyte, wherein the light source includes a first emitter that is actuated in a first wavelength range for emitting pulsed alternating light and a second emitter including a fluorescent substance that is excited by the pulsed first emitter to emit fluorescent light in a second wavelength range, wherein both emitters are jointly oriented towards a measuring surface of the test element.

2. The measuring system according to claim 1, wherein the alternating light has a pulse duration and the fluorescent light decays with a fluorescent life cycle, and the fluorescent life cycle is multiple times greater than the pulse duration.

3. The measuring system according to claim 1, wherein the first emitter is in the form of a light emitting diode emitting light.

4. The measuring system according to claim 3, wherein the light emitting diode is configured to emit light in the UV range.

5. The measuring system according to claim 1, wherein the second emitter is configured to be optically excited to emit visible fluorescent light.

6. The measuring system according to claim 1, wherein the second emitter is applied as a fluorescent layer to an emission surface of the first emitter.

7. The measuring system according to claim 1, wherein the detector includes a photoreceptor configured for the collective detection of the alternating and the fluorescent light.

8. The measuring system according to claim 1, wherein the detector includes two amplifying channels configured for wavelength-selective determination of measurement values.

9. The measuring system according to claim 1, wherein the detector includes a lock-in amplifier that is configured to be modulated with a pulse frequency of the alternating light for detecting an alternating light signal component generated by the alternating light.

10. The measuring system according to claim 1, wherein the detector comprises an amplifier that functions as an integrator configured to detect a composite signal generated by the alternating light and the fluorescent light.

11. The measuring system according to claim 10, wherein the detector includes a signal processor configured to determine signal components of at least one of the alternating light and the fluorescent light.

12. The measuring system according to claim 11, wherein the signal processor is configured to subtract the alternating light signal component from the composite signal to determine the signal components.

13. The measuring system according to claim 1, wherein the measuring unit is integrated in a hand-held device and the test element is configured as a disposable for single use in the hand-held device.

14. The measuring system according to claim 1, wherein the test element is coupled to the light source by an optical unit and the optical coupling can be monitored by a separate signal evaluation in one of the first and second wavelength ranges.

15. The measuring system according to claim 14, wherein the optical unit is one of a lens and an optical fiber.

16. A measuring method for determining blood glucose in a body fluid sample applied to a disposable test element, comprising:
- optically scanning the test element by a photometric measuring unit comprising a light source and a detector, wherein a first emitter of the light source is actuated in a first wavelength range to emit pulsed alternating light, and a second emitter formed by a fluorescent substance is excited in a second wavelength range by the pulsed first emitter to emit fluorescent light that is superimposed on the alternating light, wherein both emitters are jointly oriented towards a measuring surface of the test element.

17. The measuring method according to claim 16, wherein a signal component related to the alternating light is detected by a time-resolved signal detection.

18. The measuring method according to claim 16, wherein a signal component related to the alternating light is detected by a lock-in amplifier.

19. The measuring method according to claim 16, wherein in one wavelength range, a measurement value for an analyte in the sample is detected, and in the other wavelength range, a control value is detected for optical coupling of the test element to the measuring unit.

* * * * *